United States Patent [19]

Wiedenmann et al.

[11] Patent Number: 5,556,774
[45] Date of Patent: Sep. 17, 1996

[54] SELECTIVE DETECTION OF VIABLE AND INFECTIOUS CRYPTOSPORIDIUM OOCYSTS WITH THE HELP OF THE POLYMERASE CHAIN REACTION (PCR)

[76] Inventors: Albrecht Wiedenmann, Waldackerweg 75/1, D-73732 Esslingen; Renata Filkorn, Justinus Kerner Str. 19, D-72622 Nuertingen, both of Germany

[21] Appl. No.: 401,232

[22] Filed: Mar. 14, 1995

[30] Foreign Application Priority Data

Mar. 16, 1994 [DE] Germany .................... 44 08 700.4

[51] Int. Cl.⁶ .................... C12P 19/34; C12Q 1/68; C07H 21/04
[52] U.S. Cl. .................... 435/91.2; 435/6; 536/24.3; 536/24.32
[58] Field of Search .................... 435/6, 91.2, 24.3; 424/94.1; 536/24.3, 0.32

[56] References Cited

PUBLICATIONS

C. E. Chrisp and M. LeGendre, Folia Parasitologica 41:97–100.
Laxer et al., Am. J. Trop. Med. Hyg 45: 688–694.
Johnson et al. Wat. Sci. Tech. 27: 77–84.

*Primary Examiner*—W. Gary Jones
*Assistant Examiner*—Dianne Rees

[57] ABSTRACT

With the help of PCR it is possible to detect parasites of the genus Cryptosporidium by amplifying specific gene sequences. The disadvantage of this method is that it does not allow a statement about whether the detected gene sequences have been derived from viable and infectious parasites or from dead organisms or even from free DNA which has been released from organisms which have already disintegrated. However, by the combination of PCR with other known methods, i.e. an in vitro excystation assay and the removing or the destruction of nucleic acids which might be present in a sample material outside of Cryptosporidium oocysts before excystation this problem can be solved. Due to this combination the result of a PCR for Cryptosporidium allows a judgement on the infectivity of the examined material which would not be possible without this combination. Thus the fundamental advantages of PCR (high sensitivity and specificity, objective results, possibility of processing several samples in parallel) become available for applications in the field of environmental and food hygiene where it is essential to be able to answer the question whether a sample material is infectious or not.

2 Claims, No Drawings

SELECTIVE DETECTION OF VIABLE AND INFECTIOUS CRYPTOSPORIDIUM OOCYSTS WITH THE HELP OF THE POLYMERASE CHAIN REACTION (PCR)

LITERATURE

Davis, L. G.; M.D. Dibner and J. F. Battey: Basic Methods in Molecular Biology. Elsevier, N.Y. (1986).

Filkorn, R.; A. Wiedenmann and K. Botzenhart: Selective Detection of Viable Cryptosporidium Oocysts by PCR. Zentralblatt far Hygiene und Umweltmedizin, Gustav Fischer Verlag Stuttgart, 195 (1994) 489–494.

Johnson, D. W.; N. J. Pieniazek and J. B. Rose: DNA Probe Hybridization and PCR Detection of Cryptosporidium compared to Immunofluorescence Assay. Wat. Sci. Tech. Vol. 27, No. 3–4, (1993) 77–84.

Laxer, M. A.; B. K. Timblin and R. J. Patel: DNA sequences for the specific detection of Cryptosporidium parvum by the polymerase chain reaction. Am. J. Trop. Med. Hyg. 42 (1990) 688–694.

Wagner, C. and P. Kimmig: Vitalitätstest für Cryptosporidium parvum. Methode und praktische Anwendung. In: Bericht des 4. Hohenheimer Seminars: "Aktuelle Zoonosen", Deutsche Veterinärmedizinische Gesellschaft, Giessen (1992) 189–203.

DETAILED DESCRIPTION

1. Field of the invention

Microbiological detection method applicable in environmental and food hygiene.

2. Description of the Prior Art

For the detection of Cryptosporidium specific sequences of the nucleic acids of these parasites can be amplified using the polymerase chain reaction (PCR). Amplifiable sequences of these nucleic acids can be made available for PCR by breaking up the Cryptosporidium oocysts and the sporozoites inside them by various chemical, biochemical or physical methods (for example by application of NaOCl, proteinase K, freeze and thaw etc.) in order to release the nucleic acids (Johnson et al., 1993; Laxer et al., 1990).

The methods which have been previously described so far have the disadvantage that they can also lead to the detection of nucleic acids inside of dead or inactivated Cryptosporidium oocysts as well as to the detection of free nucleic acids of organisms which have already disintegrated beforehand. In this case a positive PCR signal cannot be used to judge whether the sample material which has been examined can cause infectious diseases or not (Filkorn et al., 1994). However, in microbiological food control and especially in the control of disinfected or differently treated drinking water a judgement on infectivity is essential.

SUMMARY OF THE INVENTION

Technical problem:

With the help of PCR it is possible to detect parasites of the genus *Cryptosporidium* by amplifying specific parts of their nucleic acids. The disadvantage of this method is that it does not allow a statement about whether the detected gene sequences have been derived from viable and infectious parasites or from dead organisms or even from free DNA which has been released from organisms which have already been disintegrated.

The problem consists in modifying the detection method in a way that a positive PCR signal occurs only in those cases when in fact viable and infectious organisms are present in the sample material.

Solution of the problem:

The solution of the problem consists in a not yet described combination of PCR with other known methods. To the sample material or to the oocysts isolated from such a material there are added substances which simulate the physiological environment in the human or animal digestive system, for example HCl, human or animal gall acids or their salts or components of the pancreas secretion. This causes the viable infectious organisms (Cryptosporidium sporozoites) to actively penetrate the oocyst wall. This means that in vitro there happens an active excystation just like it would happen in a natural infection of the intestines (Wagner and Kimmig, 1992). The free sporozoites can now be separated from the remaining oocyst material, for example by immunomagnetic methods, and then be submitted to PCR, or they are broken up by a method that leaves the remaining inactive or dead oocysts intact and releases the nucleic acids from only the actively excysted sporozoites for the following PCR detection. Such methods can be, for example, heating, treatment with proteolytic enzymes and so on. If there is a possibility that in the sample material which has to be examined or in an extract of that sample material, which contains the oocysts, nucleic acids of Cryptosporidium can already occur outside of oocysts before the excystation protocol is performed, then these nucleic acids are destroyed or removed before excystation, for example by addition of a DNAse (Davis et al., 1986)

FIELD OF APPLICATION

The method is applicable for the selective detection of viable and infectious *Cryptosporidium oocysts* in environmental and food samples, especially for their detection in drinking water and other water samples where a knowledge of the presence of infectious *Cryptosporidium oocysts* is essential.

DESCRIPTION OF THE PREFERRED EMBODIMENT

Starting point for the detection method is the sample material or an extract of the sample material which contains the Cryptosporidium oocysts and which is referred to as "Cryptosporidium suspension" in the following explanations.

Example for the removing of nucleic acids which occur outside of oocysts in a Cryptosporidium suspension:

Per 10 μl of the Cryptosporidium suspension there are added 1 μl DNase 1 (Pharmacia) and 1 μl 10x enzyme buffer. The mix is incubated 2 hours at 37° C.

Example for an in vitro excystation:

The Cryptosporidium suspension is mixed 1:1 with a solution of 1.5% taurocholate, sodium salt (Merck) in normal saline and incubated 4 hours at 37° C.

Example for a way to release nucleic acids from sporozoites without destroying oocysts with intact oocyst walls:

The Cryptosporidium suspension is put into a "safe-lock-cup" (Eppendorf) and boiled at 95° C. for 15 minutes.

Example of a PCR reaction:

One can use, for example, the primers described by Laxer et al. 1990:

P1(+)5'-CCG AGT TTG ATC CAA AAA GTT ACG AA-3'

(SEQ ID NO:1)

and

P2(−)5'-TAG CTC CTC ATA TGC CTT ATT GAG TA-3'.
(SEQ ID NO:2)

The PCR-mix may be composed like that: 10 µl 10× PCR-buffer (100 mM Tris-Cl, pH 8,3; 500 mM KCl; 15 mM MgCl$_2$; 0,01% gelatine); 16 82 l dNTP-mix (1.25 mM each dATP, dGTP, dCTP, and dTTP); 1 µl primer 1 (100 pmol); 1 µl primer 2 (100 pmol); 2 µl DMSO (Sigma); 0.5 µl Taq-polymerase (Perkin Elmer) and 59.5 µl H$_2$O per 10 µl Cryptosporidium suspension.

The PCR cycles may look for example like that:

Part 1:

| | |
|---|---|
| Denaturing | (3 minutes at 94° C.) |
| Primer annealing | (5 minutes at 45° C.) |
| Prolongation | (1 minute at 72° C.) |
| Part 1 is performed once. | |

Part 2:

| | |
|---|---|
| Denaturing | (1 minute at 94° C.) |
| Primer annealing | (2 minutes at 57° C.) |
| Prolongation | (1 minute at 72° C.) |
| Part 2 is performed 30 times. | |

The last elongation step is extended to 5 minutes.

At the end of part 2 a 10 µl aliquot is taken from the reaction cup and used to perform a second PCR in the same way as the first one.

Detection of PCR products:

The PCR products may be detected for example by gel electrophoreses in a gel with 30% agarose and a ethidium bromide concentration of 5 µg/ml. As a marker one can use for example a Promega pGEM-DNA-marker. If the primers described by Laxer have been applied the amplified gene sequence has a length of 452 bp.

We claim:

1. A method for the detection of infectious Cryptosporidium oocysts using the polymerase chain reaction (PCR) comprising:

a) isolating oocysts from a sample material to form a *Cryptosporidium oocyst* suspension;

b) adding to said *Cryptosporidium oocyst* suspension substances or combinations of substances selected from the group consisting of HCL, human or animal gall acids or their salts, or enzymes derived from pancreatic secretions, which simulate in vitro the physiological environment of a human or animal digestive system provoking active excystation of viable and infectious sporozoites;

c) releasing nucleic acids from only said sporozoites;

d) performing PCR amplification of nucleic acids of only actively excysted sporozoites;

e) detecting PCR products as a means of detecting Infectious *Cryptosporidium oocysts*.

2. The method according to claim 1 comprising destroying or removing Cryptosporidium nucleic acids which may be present outside of the oocyst prior to excystation.

* * * * *

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 26 bases
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v i ) ORIGINAL SOURCE:
        ( A ) ORGANISM: Cryptosporidium parvum
        ( B ) STRAIN: no name mentioned
        ( C ) INDIVIDUAL ISOLATE: purified from human and bovine
            feces
        ( D ) DEVELOPMENTAL STAGE: oocyst
        ( G ) CELL TYPE: Protozoan parasite ( v i i ) IMMEDIATE SOURCE: synthesized by Pharmacia ( v i i i ) POSITION IN GENOME:
        ( A ) CHROMOSOME/SEGMENT: Cryptosporidium parvum DNA
            segment A
        ( B ) MAP POSITION: base 444-469
        ( C ) UNITS: nucleotide number of a 1054-base segment
            described by Laxer et al.
                ( s e e  p u b l i c a t i o n  i n f o r m a t i o n  b e l o w )

( i x ) FEATURE:
        ( D ) OTHER INFORMATION: primer 1 for PCR ( x ) PUBLICATION INFORMATION:
        ( A ) AUTHORS: Laxer, Marc A.; Timblin, Barbara K.;
            Patel, Rubina J.
        ( B ) TITLE: DNA sequences for the specific detection of
            Cryptosporidium parvum by the polymerase chain
            reaction
        ( C ) JOURNAL: American Journal of Tropical Medicine and
            Hygiene
        ( D ) VOLUME: 45
        ( E ) ISSUE: (6)
        ( F ) PAGES: 688-694

(G) DATE: 1991

(xi) SEQUENCE DESCRIPTION: SEQ ID NO: 1:

CCGAGTTTGA TCCAAAAAGT TACGAA    26

(2) INFORMATION FOR SEQ ID NO: 2:

(i) SEQUENCE CHARACTERISTICS:
        (A) LENGTH: 26 bases
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: yes (vi) ORIGINAL SOURCE:
        (A) ORGANISM: Cryptosporidium parvum
        (B) STRAIN: no name mentioned
        (C) INDIVIDUAL ISOLATE: purified from human and bovine
            feces
        (D) DEVELOPMENTAL STAGE: oocyst
        (G) CELL TYPE: Protozoan parasite (vii) IMMEDIATE SOURCE: synthesized by Pharmacia (viii) POSITION IN GENOME:
        (A) CHROMOSOME/SEGMENT: Cryptosporidium parvum DNA
            segment A
        (B) MAP POSITION: base 870-895
        (C) UNITS: nucleotide number of a 1054-base DNA segment
            described by Laxer et al.
            (see publication information below)

(ix) FEATURE:
        (D) OTHER INFORMATION: primer 2 for PCR (x) PUBLICATION INFORMATION:
        (A) AUTHORS: Laxer, Marc A.; Timblin, Barbara K.;
            Patel, Rubina J.
        (B) TITLE: DNA sequences for the specific detection of
            Cryptosporidium parvum by the polymerase chain
            reaction
        (C) JOURNAL: American Journal of Tropical Medicine and
            Hygiene
        (D) VOLUME: 45
        (E) ISSUE: (6)
        (F) PAGES: 688-694
        (G) DATE: 1991

(xi) SEQUENCE DESCRIPTION: SEQ ID NO: 2:

TAGCTCCTCA TATGCCTTAT TGAGTA    26